(12) United States Patent
Newns (10) Patent No.: US 10,136,676 B2
(45) Date of Patent: Nov. 27, 2018

(54) ELECTRONIC VAPOR PROVISION SYSTEM (71) Applicant: NICOVENTURES HOLDINGS LIMITED, London (GB)

(72) Inventor: David Newns, London (GB)

(73) Assignee: NICOVENTURES HOLDINGS LIMITED, London (GB)

( * ) Notice: Subject to any disclaimer, the term of this patent is extended or adjusted under 35 U.S.C. 154(b) by 0 days.

(21) Appl. No.: 15/501,452

(22) PCT Filed: Aug. 5, 2015

(86) PCT No.: PCT/GB2015/052261
§ 371 (c)(1),
(2) Date: Feb. 3, 2017

(87) PCT Pub. No.: WO2016/020675
PCT Pub. Date: Feb. 11, 2016

(65) Prior Publication Data
US 2017/0231284 A1    Aug. 17, 2017

(30) Foreign Application Priority Data
Aug. 5, 2014    (GB) .................................. 1413835.8

(51) Int. Cl.
*A24F 11/00* (2006.01)
*A24F 47/00* (2006.01)
*H05B 1/02* (2006.01)

(52) U.S. Cl.
CPC ......... *A24F 47/008* (2013.01); *H05B 1/0244* (2013.01); *H05B 2203/021* (2013.01)

(58) Field of Classification Search
CPC ... A24F 47/008; A24F 47/006; H05B 1/0244; H05B 2203/021; F01K 5/00
(Continued)

(56) References Cited

U.S. PATENT DOCUMENTS 8,495,998 B2    7/2013    Schennum
8,689,786 B2    4/2014    Schennum
(Continued)

FOREIGN PATENT DOCUMENTS

CN    103948177 A    7/2014
EP    1618803 A1    1/2006
(Continued)

OTHER PUBLICATIONS

Russian Decision to Grant, Application No. 2017103525, dated Mar. 20, 2018, 12 pages.
(Continued)

*Primary Examiner* — Jean F Duverne
(74) *Attorney, Agent, or Firm* — Patterson Thuente Pedersen, P.A.

(57) ABSTRACT

Some embodiments provide an electronic vapor provision system including a vaporizer for vaporizing liquid for inhalation by a user of the electronic vapor provision system; a power supply comprising a cell or battery for supplying power to the vaporizer; a sensor for detecting airflow through the electronic vapor provision system as a result of the inhalation by the user; a manual activation device; and a control unit for causing power to be supplied to the vaporizer to vaporize the liquid providing the control unit determines that both (i) the sensor is detecting airflow through the electronic vapor provision system and (ii) the manual activation device has been manually activated by the user.

11 Claims, 4 Drawing Sheets

(58) Field of Classification Search
USPC .......................................................... 131/328
See application file for complete search history.

(56) References Cited

U.S. PATENT DOCUMENTS

| | | |
|---|---|---|
| 8,950,395 B2 | 2/2015 | Schennum |
| 2008/0092912 A1 | 4/2008 | Robinson |
| 2011/0226236 A1 | 9/2011 | Buchberger |
| 2011/0238010 A1 | 9/2011 | Kirschenman |
| 2012/0174914 A1 | 7/2012 | Pirshafiey |
| 2012/0260926 A1 | 10/2012 | Tu |
| 2013/0220315 A1 | 8/2013 | Conley |
| 2014/0096781 A1 | 4/2014 | Sears |
| 2016/0213065 A1* | 7/2016 | Wensley ............... A24F 47/008 |
| 2016/0331035 A1* | 11/2016 | Cameron .................. F01K 5/00 |
| 2017/0079329 A1* | 3/2017 | Zitzke ................... A24F 47/008 |
| 2017/0135412 A1* | 5/2017 | Cameron ............. A24F 47/008 |
| 2017/0222468 A1* | 8/2017 | Schennum .............. H02J 7/025 |

FOREIGN PATENT DOCUMENTS

| | | |
|---|---|---|
| GB | 2507103 A | 4/2014 |
| JP | 2014512207 | 5/2014 |
| KR | 20110132290 A | 12/2011 |
| KR | 10-1162688 | 7/2012 |
| KR | 10-1233985 | 2/2013 |
| KR | 10-1285219 | 7/2013 |
| RU | 138386 U1 | 3/2014 |
| WO | WO9501137 A1 | 1/1995 |
| WO | WO2004080216 A1 | 9/2004 |
| WO | WO2012114322 | 8/2012 |
| WO | WO2013138384 A2 | 9/2013 |
| WO | WO2013159245 A1 | 10/2013 |
| WO | WO2014058678 | 4/2014 |

OTHER PUBLICATIONS

Korean Office Action, Application No. 10-2017-7003144, dated Mar. 21, 2018, 7 pages (13 pages with translation).
Canadian Office Action, Application No. 2,955,142, dated Nov. 29, 2017, 4 pages.
Japanese Office Action, Application No. 2017-506276, dated Dec. 5, 2017, 4 pages (7 pages with translation).
International Search Report, International Application No. PCT/GB2015/052261, dated May 11, 2015, 4 pages.
International Preliminary Report on Patentability, International Application No. PCT/GB2015/052261, dated Nov. 22, 2016, 9 pages.
GB Search Report, Application No. GB1413835.8, dated Feb. 4, 2015, 4 pages.
Chinese Office Action, Application No. 201580041869.3, dated Sep. 11, 2018, 7 pages.

* cited by examiner

ELECTRONIC VAPOR PROVISION SYSTEM

CROSS-REFERENCE TO RELATED APPLICATIONS

The present application is a National Phase entry of PCT Application No. PCT/GB2015/052261, filed Aug. 5, 2015, which claims priority from GB Patent Application No. 1413835.8, filed Aug. 5, 2014, each of which is hereby fully incorporated herein by reference.

TECHNICAL FIELD

The present disclosure relates to electronic vapor provision systems such as electronic nicotine delivery systems (e.g. e-cigarettes).

BACKGROUND

Electronic vapor provision systems such as e-cigarettes generally contain a reservoir of liquid, typically nicotine, which is to be vaporized or otherwise converted into an aerosol. Such devices are usually provided with one or more air inlet holes located away from the mouthpiece. When a user sucks on the mouthpiece, air is drawn in through the inlet holes and past the vapor source, such as a heater supplied with nicotine or other liquid from a cartridge.

Some e-cigarettes are provided with a specific manual activation facility, such as a button which is used to activate the heater. In such devices, the heater is only activated while the user is holding down the button. However, such a manual activation facility may be activated accidently, for example, if something presses against the button while the device is located in a user's pocket. This can then cause the heater to become activated unintentionally, often without the user's knowledge, which will generally waste battery power, and may also cause damage to the heater and/or injury to the user.

An existing solution to such a problem is to providing such devices with a more complex activation mechanism so that it is difficult to activate accidently. For example, a device may have a button which requires a certain number of consecutive presses by the user in order for activation of the heater to occur. However, such relatively complicated mechanisms are generally more inconvenient and cumbersome for a user.

Another approach adopted by some devices for avoiding accidental activation is to have the heater activated automatically by an airflow sensor (such as a pressure drop sensor) which detects airflow through the device as the user inhales on the device. More particularly, when a user inhales on the device, the heater is activated to vaporize a small amount of liquid, which is therefore inhaled by the user. However, this allows the heater (and hence the e-cigarette) to be activated by someone other than an intended user, who picks up the e-cigarette and mimics the action of inhalation.

The approach described herein seeks to help address the above-mentioned problems.

SUMMARY

An electronic vapor provision system is provided comprising a vaporizer for vaporizing liquid for inhalation by a user of the electronic vapor provision system; a power supply comprising a cell or battery for supplying power to the vaporizer; a sensor for detecting airflow through the electronic vapor provision system as a result of the inhalation by the user; a manual activation device; and a control unit for causing power to be supplied to the vaporizer to vaporize the liquid providing the control unit determines that both (i) the sensor is detecting airflow through the electronic vapor provision system and (ii) the manual activation device has been manually activated by the user.

The approach described herein is not restricted to specific embodiments such as set out below, but includes and contemplates any appropriate combinations of features presented herein. For example, an electronic vapor provision system may be provided in accordance with the approach described herein which includes any one or more of the various features described below as appropriate.

BRIEF DESCRIPTION OF THE DRAWINGS

Various embodiments of the disclosure will now be described in detail by way of example only with reference to the following drawings.

DETAILED DESCRIPTION

As described above, the present disclosure relates to an electronic vapor provision system, such as an e-cigarette. Throughout the following description the term "e-cigarette" is used; however, this term may be used interchangeably with electronic vapor provision system.

Figure 1:
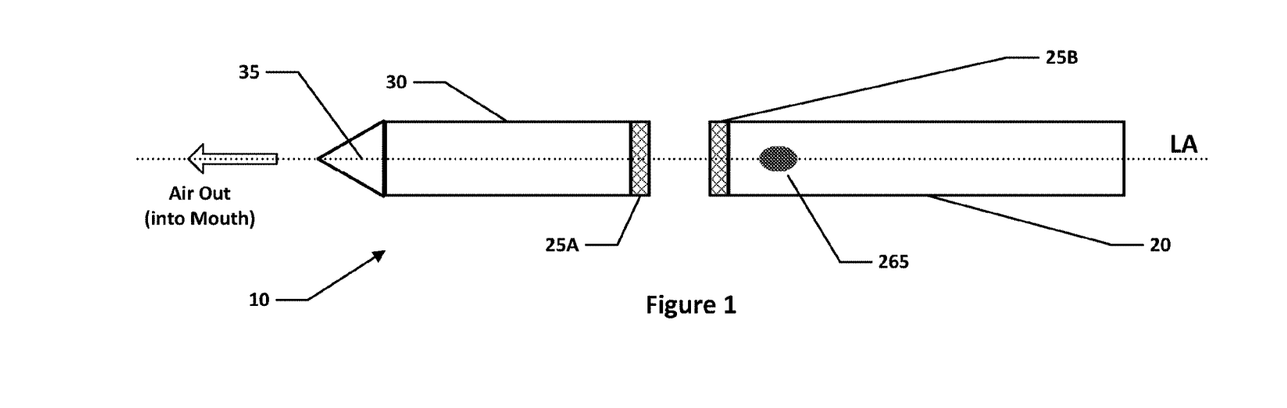
FIG. 1 is a schematic (exploded) diagram of an electronic vapor provision system such as an e-cigarette in accordance with some embodiments of the disclosure.

FIG. 1 is a schematic diagram of an electronic vapor provision system such as an e-cigarette 10 in accordance with some embodiments of the disclosure (not to scale). The e-cigarette has a generally cylindrical shape, extending along a longitudinal axis indicated by dashed line LA, and comprises two main components, namely a body 20 and a cartomizer 30. The cartomizer 30 includes an internal chamber containing a reservoir of nicotine, a vaporizer (such as a heater), and a mouthpiece 35. The reservoir may be a foam matrix or any other structure for retaining the nicotine until such time that it is required to be delivered to the vaporizer. The vaporizer is for vaporizing the nicotine, and the cartomizer 30 may further include a wick or similar facility to transport a small amount of nicotine from the reservoir to a vaporizing location on or adjacent the vaporizer. In the following, a heater is used as a specific example of a vaporizer. However, it will be appreciated that other forms of vaporizer (for example, those which utilize ultrasonic waves) could also be used.

The body 20 includes a re-chargeable cell or battery to provide power to the e-cigarette 10 and a circuit board for generally controlling the e-cigarette 10. When the heater receives power from the battery, as controlled by the circuit board, the heater vaporizes the nicotine and this vapor is then inhaled by a user through the mouthpiece 35. The body 20 is further provided with a manual activation device 265, e.g. a button, switch, or touch sensor located on the outside of the body 20, as described in more detail below.

The body 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector 25B on the body 20 that is used to connect to the cartomizer 30 also serves as a socket for connecting a charging device (not shown) when the body 20 is detached from the cartomizer 30. The other end of the charging device can be plugged into a USB socket to re-charge the cell in the body 20 of the e-cigarette 10. In other implementations, a cable may be provided for direct connection between the electrical connector 25B on the body 20 and a USB socket.

The e-cigarette 10 is provided with one or more holes (not shown in FIG. 1) for air inlet. These holes connect to an air passage through the e-cigarette 10 to the mouthpiece 35. When a user inhales through the mouthpiece 35, air is drawn into this air passage through the one or more air inlet holes, which are suitably located on the outside of the e-cigarette 10. This airflow (or the resulting change in pressure) is detected by a sensor unit that in turn activates the heater to vaporize the nicotine from the cartridge. The airflow passes through, and combines with, the nicotine vapor, and this combination of airflow and nicotine vapor then passes out of the mouthpiece 35 to be inhaled by a user. The cartomizer 30 may be detached from the body 20 and disposed of when the supply of nicotine is exhausted (and replaced with another cartomizer if so desired).

It will be appreciated that the e-cigarette 10 shown in FIG. 1 is presented by way of example, and various other implementations can be adopted. For example, in some embodiments, the cartomizer 30 is provided as two separable components, namely a cartridge comprising the nicotine reservoir and mouthpiece (which can be replaced when the nicotine from the reservoir is exhausted), and a vaporizer comprising a heater (which is generally retained). As another example, the charging facility may connect to an additional or alternative power source, such as a car cigarette lighter.

Figure 2:
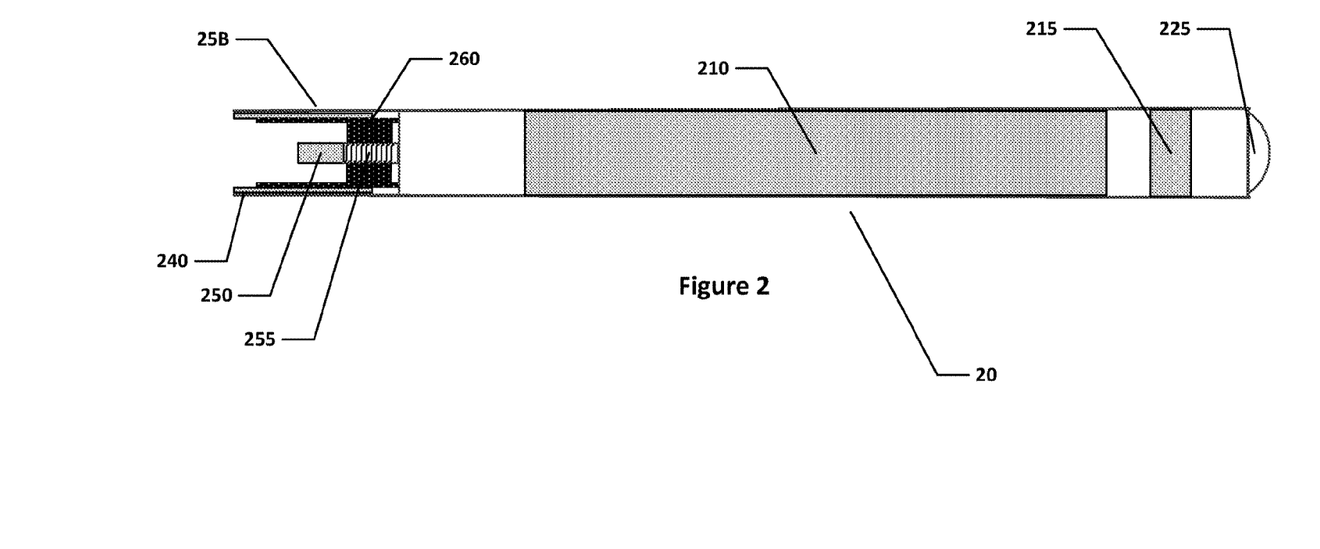
FIG. 2 is a schematic diagram of the body of the e-cigarette of FIG. 1 in accordance with some embodiments of the disclosure.

FIG. 2 is a schematic (simplified) diagram of the body 20 of the e-cigarette 10 of FIG. 1 in accordance with some embodiments of the disclosure. FIG. 2 can generally be regarded as a cross-section in a plane through the longitudinal axis LA of the e-cigarette 10. Note that various components and details of the body, e.g. such as wiring and more complex shaping, have been omitted from FIG. 2 for reasons of clarity.

The body 20 includes a battery or cell 210 for powering the e-cigarette 10, as well as a chip (not shown in FIG. 2), such as an application specific integrated circuit (ASIC) or microcontroller for controlling the e-cigarette 10. The ASIC may be positioned alongside or at one end of the battery 210. The ASIC is attached to a sensor unit 215 to detect an inhalation on mouthpiece 35 (or alternatively the sensor unit 215 may be provided on the ASIC itself).

The body 20 further includes a cap 225 to seal and protect the far (distal) end of the e-cigarette 10. There is an air inlet hole provided in or adjacent to the cap 225 to allow air to enter the body 20 and flow past the sensor unit 215 when a user inhales on the mouthpiece 35. This airflow therefore allows the sensor unit 215 to detect the user inhalation.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A of the cartomizer 30, thereby helping to ensure good electrical connectivity between the body 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B.

As mentioned above, a button 265, which represents a form of manual activation device 265, is located on the outer housing of the body 20. The button 265 may be implemented using any appropriate mechanism which is operable to be manually activated by the user—for example, as a mechanical button or switch, a capacitive or resistive touch sensor, and so on. It will also be appreciated that the manual activation device 265 may be located on the outer housing of the cartomizer 30, rather than the outer housing of the body 20, in which case, the manual activation device 265 may be attached to the ASIC via the connections 25A, 25B. The button 265 might also be located at the end of the body 20, in place of (or in addition to) cap 225.

Figure 3:
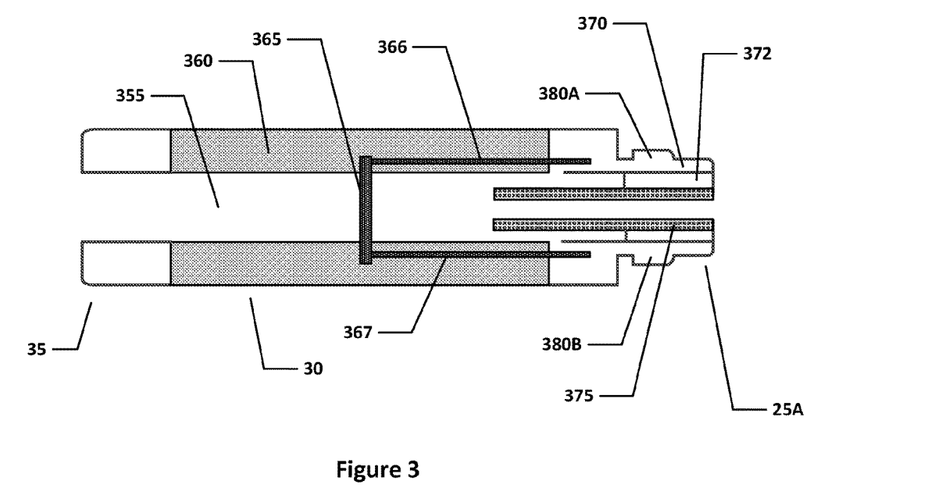
FIG. 3 is a schematic diagram of the vaporizer portion of the e-cigarette of FIG. 1 in accordance with some embodiments of the disclosure.

FIG. 3 is a schematic diagram of the cartomizer 30 of the e-cigarette 10 of FIG. 1 in accordance with some embodiments of the disclosure. FIG. 3 can generally be regarded as a cross-section in a plane through the longitudinal axis LA of the e-cigarette 10. Note that various components and details of the cartomizer 30, such as wiring and more complex shaping, have been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer 30 to the body 20. A reservoir of nicotine 360 is provided around the air passage 335. This reservoir 360 may be implemented, for example, by providing cotton or foam soaked in nicotine. The cartomizer 30 also includes a heater 365 for heating nicotine from reservoir 360 to generate nicotine vapor to flow through air passage 355 and out through mouthpiece 35 in response to a user inhaling on the e-cigarette 10. The heater 365 is powered through lines 366 and 367, which are in turn connected to opposing polarities (positive and negative, or vice versa) of the battery 210 of the main body 20 via connector 25A (the details of the wiring between the power lines 366 and 367 and connector 25A are omitted from FIG. 3).

The connector 25A includes an inner electrode 375, which may be silver-plated or made of some other suitable metal or conducting material. When the cartomizer 30 is connected to the body 20, the inner electrode 375 contacts the electrical contact 250 of the body 20 to provide a first electrical path between the cartomizer 30 and the body 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring is surrounded by the cartomizer connector 370, which may be silver-plated or made of some other suitable metal or conducting material. When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body 20 to the heater 365 in the cartomizer 30 via supply lines 366 and 367 as appropriate.

The cartomizer connector 370 is provided with two lugs or tabs 380A, 380B, which extend in opposite directions away from the longitudinal axis of the e-cigarette 10. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer 30 and body 20 are held in a fixed position relative to one another, with minimal wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
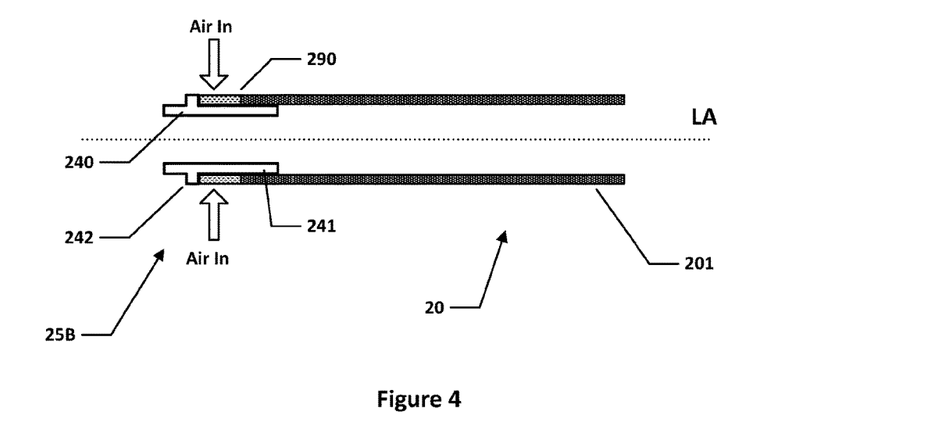
FIG. 4 is a schematic diagram showing certain aspects of one end of the body portion of the e-cigarette of FIG. 1 in accordance with some embodiments of the disclosure.

FIG. 4 is a schematic diagram of certain details of the connector 25B at the end of the body 20 in accordance with some embodiments of the disclosure (but omitting for clarity most of the internal structure of the connector as shown in FIG. 2, such as trestle 260). In particular, FIG. 4 shows the external housing 201 of the body 20, which generally has the form of a cylindrical tube. This external housing 201 may comprise, for example, an inner tube of metal with an outer covering of paper or similar. The external housing 201 may also comprise the manual activation device 265 (not shown in FIG. 4) so that the manual activation device 265 is easily accessible to the user.

The body connector 240 extends from this external housing 201 of the body 20. The body connector 240 as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette. Surrounding the shaft portion 241 of the body connector 240, where the shaft portion 241 does not overlap with the external housing 201, is a collar or sleeve 290, which is again in a shape of a cylindrical tube. The collar 290 is retained between the lip portion 242 of the body connector 240 and the external housing 201 of the body 20, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow past sensor 215 when a user inhales on the mouthpiece 35. However, the majority of air that enters the device when a user inhales flows through collar 290 and body connector 240 as indicated by the two arrows in FIG. 4.

Figure 5:
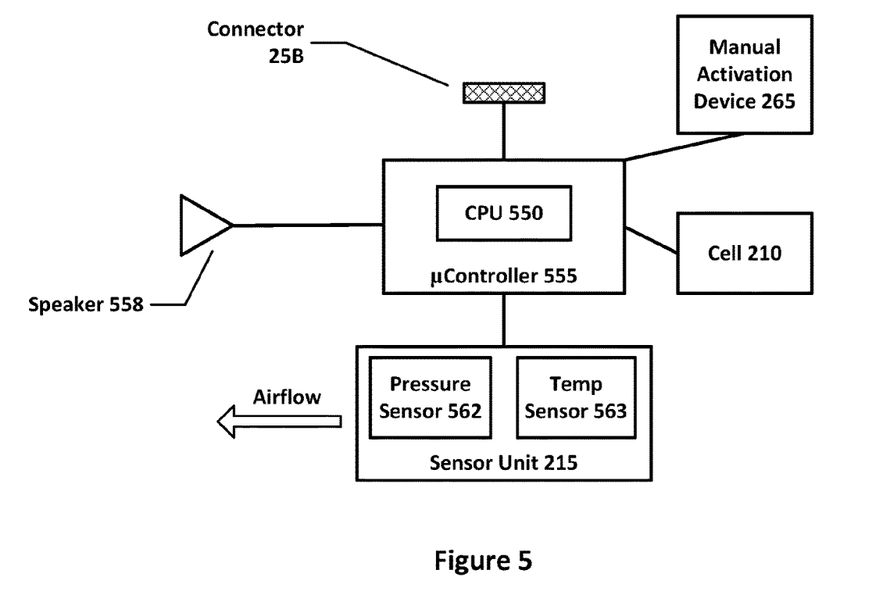
FIG. 5 is a schematic diagram of the main functional components of the body of the e-cigarette of FIG. 1 in accordance with some embodiments of the disclosure.

FIG. 5 is a schematic diagram of the main functional components of the body 20 of the e-cigarette 10 of FIG. 1 in accordance with some embodiments of the disclosure. These components may be mounted on the circuit board provided within the body 20, although depending on the particular configuration, in some embodiments, one or more of the components may instead be accommodated in the body 20 to operate in conjunction with the circuit board, but is/are not physically mounted on the circuit board itself.

The body 20 includes the sensor unit 215 located in or adjacent to the air path through the body 20 from the air inlet to the air outlet (to the vaporizer). The sensor unit 215 includes a pressure drop sensor 562 and temperature sensor 563 (also in or adjacent to this air path). It will be appreciated, however, that the sensor unit 215 may include the pressure drop sensor 562 without the temperature sensor 563 or may include an airflow monitor to directly measure airflow (rather than pressure drop). The body 20 also includes the manual activation device 265. The body 20 further includes a small speaker 558 and an electrical socket or connector 25B for connecting to the cartomizer 30 or to a USB charging device.

The microcontroller (e.g. an ASIC) 555 includes a CPU 550. The operations of the CPU 550 and other electronic components, such as the pressure sensor 562, are generally controlled at least in part by software programs running on the CPU 550 (or other component). Such software programs may be stored in non-volatile memory, such as ROM, which can be integrated into the microcontroller 555 itself, or provided as a separate component. The CPU 550 may access the ROM to load and execute individual software programs as and when required. The microcontroller 555 also contains appropriate communications interfaces (and control software) for communicating as appropriate with other devices in the body 10, such as the pressure sensor 562 and manual activation device 265.

The CPU 550 controls the speaker 558 to produce audio output to reflect conditions or states within the e-cigarette 110, such as a low battery warning. Different signals for signaling different states or conditions may be provided by utilizing tones or beeps of different pitch and/or duration, and/or by providing multiple such beeps or tones.

The CPU 550 is operable to determine whether or not the manual activation device 265 has been activated by the user. Furthermore, as noted above, the e-cigarette 10 provides an air path from the air inlet through the e-cigarette 10, past the pressure drop sensor 562 and the heater (in the vaporizer or cartomizer 30), to the mouthpiece 35. Thus when a user inhales on the mouthpiece 35 of the e-cigarette 10, the CPU 550 detects such inhalation based on information from the pressure drop sensor 562. In response to both the detection of an inhalation and the determination that the manual activation device 265 has been activated, the CPU 550 supplies power to the heater, which thereby heats and vaporizes the nicotine from the wick for inhalation by the user.

In other words, the CPU 550 is responsive both to (i) detection of an inhalation on the mouthpiece 35 by the sensor unit 215 and to (ii) manual activation of the manual activation device 265 by the user pressing or touching this device as appropriate. In response to receiving (i) and (ii) together (i.e. in combination with one another, rather than either one individually), the ASIC or CPU then provides power from the battery or cell 210 to the heater in the cartomizer 30 to vaporize liquid into the airflow which is inhaled by a user. Thus the heater is activated only when the ASIC determines that both the sensor unit 215 is detecting airflow through the e-cigarette 10 and also that the manual activation device 265 has been manually activated by the user. This two-fold control mechanism reduces the risk that the heater is unintentionally activated, in that if the manual activation device 265 is accidently pressed or touched when the user is not inhaling on the mouthpiece 35, the heater will not be activated. Conversely, when the user does wish to activate the heater (so as to inhale the liquid vapor), the user inhales on the mouthpiece 35 and presses (or touches, slides or rotates, etc) the manual activation device 265 to activate the heater.

The activation time resulting from such a pressing of the manual activation device 265 may have a preset value, such as a few seconds, to allow a desired amount of liquid vapor to be provided to the user. Alternatively, the heater may remain activated, thus heating the liquid, for as long as the user both inhales on the mouthpiece 35 and keeps the manual activation device 265 activated. This is a very easy-to-use mechanism and gives the user control as to how much liquid vapor is provided to them during an inhaling period.

Figure 6:
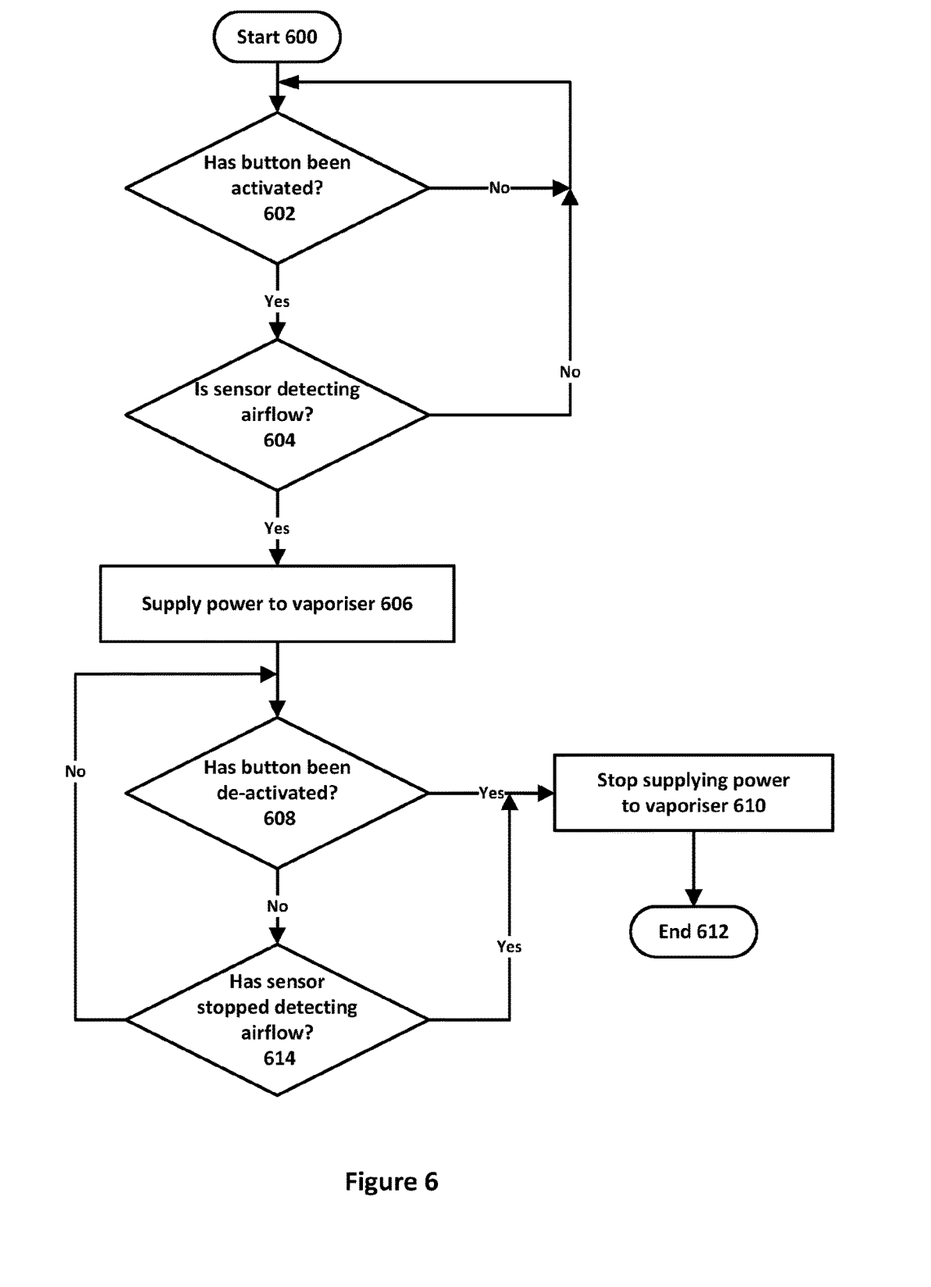
FIG. 6 is a schematic flowchart which illustrates certain aspects of operation of the e-cigarette of FIG. 1 in accordance with some embodiments of the disclosure.

FIG. 6 shows a flow chart illustrating a process performed by the microcontroller 555 for controlling operation of the electronic vapor provision system according to some embodiments of the present disclosure.

The process starts at 600. At 602, it is determined whether or not the manual activation device 265 has been manually activated by the user. If the manual activation device 265 has not been activated, then the process returns to the beginning of 602. On the other hand, if the activation device 265 has been activated, then the process moves on to 604, in which it is determined whether or not the sensor unit 215 is detecting an airflow through the e-cigarette 10. The microcontroller 555 determines that the sensor unit 215 is detecting an airflow when the airflow is greater than or equal to a threshold value (as determined by a threshold pressure drop value measure by the pressure drop sensor 562, for example). If the sensor unit 215 is not detecting an airflow, then the process returns to the beginning of 602. On the other hand, if the sensor unit 215 is detecting an airflow, then the process moves onto 606. At 606, the microcontroller 555 causes power to be supplied to the vaporizer (such as heater 365). This activates the vaporizer and causes the liquid of the cartomizer 30 to be vaporized for inhalation by the user.

The process then moves on to 608, in which it is determined whether or not the manual activation device 265 has been deactivated. Depending upon the particular design of the button or other manual activation device, such deactivation may occur through various circumstances—e.g. because a predetermined time has now elapsed since the button was last pressed (activated); because the user is no longer pushing or touching the button; or because the user has returned the button (or allowed the button to return) from an "on" position to an "off" position.

If it is determined at 608 that the manual activation device 265 has been deactivated, then the process moves onto 610.

At 610, the microcontroller 555 stops power from being supplied to the vaporizer, thus deactivating the vaporizer. The process then ends at 612. On the other hand, if is determined at 608 that the manual activation device 265 has not been deactivated, then the process moves on to 614, in which it is determined whether or not the sensor unit 215 has stopped detecting the airflow. The microcontroller 555 generally determines that the sensor unit 215 has stopped detecting an airflow when the airflow has become less than the threshold value. However, the sensor 215 and/or the microcontroller 555 may apply one or more other detection criteria. For example, the detection of the airflow may be regarded as having stopped if the airflow falls below a threshold value for a predetermined period of time, or if the rate of decline of airflow is above a certain level at the time that the threshold value is crossed. The skilled person will be aware of other possible detection criteria (or combinations thereof). If the sensor unit 215 has stopped detecting the airflow at 614, then the process moves on to 610 so as to stop power from being supplied to the vaporizer, thus deactivating the vaporizer. The process then ends at 612. On the other hand, if it is determined at 614 that the sensor unit has not stopped detecting the airflow, then the process returns to the beginning of 608.

Note that although FIG. 6 shows two pairs of tests (602 and 604; then 608 and 614) being performed sequentially, in practice one or both of the pairs of tests may be performed in parallel—i.e. 602 with 604 and/or 608 with 614. For example, the microcontroller may receive separate (parallel) inputs from the sensor 215 and the manual activation device 265 which can be combined using an AND gate (or equivalent processing logic). Thus when the sensor 215 and the manual activation device 265 both make a positive detection/activation, the output from the AND gate is likewise positive, and the microcontroller supplies power to the vaporizer as per 606. However, if either (or both) of the inputs from the sensor 215 and the manual activation device 265 stops being positive (i.e. no airflow or no activation respectively), then the output from the AND gate goes negative, and hence the microcontroller stops supplying power to the vaporizer as per 610 (or does not start supplying such power).

Thus, it can be seen from FIG. 6 that power is provided to the vaporizer only when the microcontroller 555 determines that both the sensor unit 215 is detecting airflow through the e-cigarette 10 and the manual activation device 265 has been manually activated by the user. This helps to prevents the vaporizer from being unintentionally activated by the user, since even if the manual activation device 265 is accidently activated by the user, the user will not be inhaling on the mouthpiece 35 and therefore the vaporizer will not be activated. At the same time, when the user does wish to activate the vaporizer (so as to inhale the liquid vapor), the user inhales on the mouthpiece 35 and activates the manual activation device 265 to activate the vaporizer for an amount time suitable to allow a desired amount of liquid vapor to be provided to the user.

In general terms, the vaporizer remains activated, thus vaporizing the liquid, as long as the user both inhales on the mouthpiece 35 and keeps the manual activation device 265 activated. This is an easy-to-use and intuitive mechanism, which does not require the user to learn any complicated set of operations for the button 265.

In addition, user may be able to control how much liquid vapor is provided to them during a puff of the e-cigarette 10. For example, if the manual activation device 265 remains activated for as long as a user's finger is in contact with a button or similar detection device 265, this allows the user to control directly the amount of time for which the heater is activated, and thus the period (duration) of the vapor delivery. Accordingly, a user who desires a reduced level of vapor delivery may press the button say, for only half the inhaling period, and thereby receive a reduced amount of vapor. It will be appreciated that other forms of manual activation device 265 may provide analogous forms of user control.

As previously mentioned, different embodiments may adopt different implementations of the manual activation device 265. For example, the manual activation device 265 may be a physical button or switch or may be a touch sensor (such as a resistive or capacitive touch sensor) which is activated simply by being touched by the user. In addition, the method of activating and deactivating the manual activation device 265 may also take a range of different approaches. For example, in some cases the manual activation device may be activated for a predetermined period of time after the button 265 is pressed or touched, after which the manual activation device is de-activated. Such an implementation helps to ensure that the manual activation device is de-activated after user, although the user does not have full (direct) control over the supply of power to the vaporizer.

In some embodiments, the manual activation device 265 comprises a button which is activated by a first press of the button by the user, and then deactivated by a second (subsequent) press of the button by the user. In other words, alternate presses of the button activate and then deactivate the manual activation device. During the time period between the first and second press, the microcontroller regards the manual activation device 265 as activated. This method has the advantage of providing the user with direct control over the duration of activation, although the manual activation device may remain activated if the user forgets or neglects to make a second press. In another example, the manual activation device 265 is deemed activated for as long as the button is continuously pressed by the user. This method again gives the user direct control over how long the vaporizer is activated during an inhalation period. Moreover, it is natural for a user to stop pressing the button 265 when they have finished using the e-cigarette 10, so it is unlikely that the manual activation device would remain in an activated state unintentionally.

Similar methods may also be adopted when the manual activation device 265 comprises a touch sensor. That is, in one example, the manual activation device 265 is deemed to be activated following a first touch of the touch sensor by the user and then deemed to be deactivated following a second touch of the touch sensor by the user. During the time period between the first and second touch, the manual activation device 265 is deemed activated. In another example, the manual activation device 265 is deemed activated for as long as the touch sensor is continuously touched by the user.

In another example, if the manual activation device 265 comprises a manual switch, such as a slidable or rotatable switch, then the manual activation device 265 will be activated when the switch is put into an "on" position and deactivated when the switch is put into an "off" position. In such embodiments, the switch may be biased towards the "off" position so that the user has to continually hold the switch in the "on" position in order for the manual activation device to be activated. In this case, when the user stops holding the switch in the "on" position, the switch will automatically return (under the influence of a spring or some other resilient bias mechanism, etc) to the "off" position.

This not only makes it more difficult for the switch to be unintentionally retained in the "on" (activated) position, but also makes it easier for the user, since the user does not have to manually change the switch back to the "off" position after inhaling on the e-cigarette 10.

The manual activation device 265, be it a button, touch sensor, switch or any other suitable device, is generally positioned such that it is easily accessible to the user when the user holds the e-cigarette 10 so as to inhale on it. For example, the manual activation device 265 may be located somewhat closer to the proximal (mouth) end of the e-cigarette than to the distal (cap) end of the e-cigarette 10, since the user is more likely to hold the e-cigarette 10 closer at a position closer to its proximal end (as is the case for conventional combustible cigarettes). Thus in the example shown in FIG. 1, the button 265 is located on the body portion 25 (since the cartridge 30 is disposable), but at the end nearest to the mouthpiece 35. The button may be activated (pressed, moved or touched) conveniently while the e-cigarette 10 is being held by a user.

It will be appreciated that the manual activation device described herein may require an ongoing, continuous operation from the user for the activation to remain effective; once the user operation terminates, then the manual activation (automatically) terminates, i.e. is de-activated. For example, a touch button may be activated only for as long as the user touches the button, and hence is no longer active as soon as the user stops touching a button. Similarly, a press button may remain activated only for as long as a user continues to press the button, after which the button returns automatically to the de-activated position. This type of manual activation device gives a user very direct control over the operation of an e-cigarette 10.

In another example of a manual activation device described herein, the activation may remain effective for a limited (typically predetermined) time following a user action. As an example, a manual activation device may comprise a button, and after user touches or presses this button, the manual activation device remains active for a predetermined time (e.g. several seconds) after the button has been touched or pressed. At the expiry of the predetermined time, the manual activation device is then automatically deactivated. This approach avoids the risk that an e-cigarette 10 is accidentally left in an activated state.

The approach described herein can be extended to a range of electronic vapor provision systems, including, for example, the type of inhaler described in US 2011/0226236, and also heat-not-burn devices (which may include some plant matter or extract, for example, tobacco leaf, which is then heated or provided with steam to produce the desired vapor) that likewise include an electronic vaporizer.

In order to address various issues and advance the art, this disclosure shows by way of illustration various embodiments in which that which is claimed may be practiced. The advantages and features of the disclosure are of a representative sample of embodiments only, and are not exhaustive and/or exclusive. They are presented only to assist in understanding and to teach that which is claimed. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc other than those specifically described herein. The disclosure may include other inventions not presently claimed, but which may be claimed in future.

The invention claimed is:

1. An electronic vapor provision system comprising:
a vaporizer for vaporizing liquid for inhalation by a user of the electronic vapor provision system;
a re-chargeable power supply comprising a cell or battery for supplying power to the vaporizer, wherein the cell or battery is configured to be re-chargeable solely from a power source external to the electronic vapor provision system;
a sensor for detecting airflow through the electronic vapor provision system as a result of the inhalation by the user;
a manual activation device; and
a control unit for causing power from the cell or battery to be supplied to the vaporizer to vaporize the liquid providing the control unit determines that both (i) the sensor is detecting airflow through the electronic vapor provision system and (ii) the manual activation device is manually activated by the user,
wherein the manual activation device is configured to remain activated only for the duration of an ongoing, continuous operation from the user, and once the user operation terminates, the manual activation device is configured to automatically de-activate.

2. The electronic vapor provision system of claim 1, wherein the vaporizer is a heater which is supplied with power from the power supply to heat and thereby vaporize the liquid for inhalation by the user.

3. The electronic vapor provision system of claim 1, wherein the liquid comprises nicotine.

4. The electronic vapor provision system of claim 1, wherein the sensor detects a pressure drop to detect airflow through the electronic vapor provision system.

5. The electronic vapor provision system of claim 1, wherein the manual activation device comprises a button.

6. The electronic vapor provision system of claim 1, wherein the manual activation device is a touch sensor.

7. The electronic vapor provision system of claim 1, wherein the manual activation device is a slidable or rotatable switch for movement between a first position in which the manual activation device is deactivated and a second position in which the manual activation device is activated.

8. The electronic vapor provision system of claim 7, wherein the switch is biased towards the second position in which the manual activation device is deactivated.

9. The electronic vapor provision system of claim 1, wherein the sensor is mounted on a circuit board.

10. A method of operating an electronic vapor provision system including a vaporizer for vaporizing liquid for inhalation by a user of the electronic vapor provision system, wherein the electronic vapor provision system includes a re-chargeable power supply comprising a cell or battery for supplying power to the vaporizer, wherein the cell or battery is configured to be re-chargeable solely from a power source external to the electronic vapor provision system, the method comprising:
providing a manual activation device for user activation;
providing a sensor to detect airflow through the electronic vapor provision system as a result of the inhalation by the user; and
causing power from the cell or battery to be supplied to the vaporizer to vaporize the liquid provided that both (i) the sensor is detecting airflow through the electronic vapor provision system and (ii) the manual activation device is manually activated by the user,
wherein the manual activation device remains activated only for the duration of an ongoing, continuous operation from the user, and once the user operation terminates, the manual activation device is automatically de-activated.

11. The method of claim 10, wherein the manual activation device is a button, touch sensor, or switch.

* * * * *